United States Patent [19]

Mahoney et al.

[11] Patent Number: 5,020,532
[45] Date of Patent: Jun. 4, 1991

[54] EXHALATION VALVE FOR RESPIRATORY CIRCUIT

[75] Inventors: Michael R. Mahoney, Cucamonga, Calif.; Wayne H. Nieman, Lake Forest, Ill.; Douglas J. McDowell, Canyon Country; Virginia Krapil, Irvine, both of Calif.

[73] Assignee: Baxter International Inc.

[21] Appl. No.: 270,703

[22] Filed: Nov. 14, 1988

[51] Int. Cl.$^5$ .............................................. A62B 9/02
[52] U.S. Cl. ............................ 128/205.24; 128/204.18
[58] Field of Search ................... 128/204.18, 911, 912, 128/205.24, 204.29

[56] References Cited

U.S. PATENT DOCUMENTS

| | | | |
|---|---|---|---|
| 3,826,255 | 7/1974 | Havstad et al. | 128/194 |
| 3,933,171 | 1/1976 | Hay | 128/205.24 |
| 4,190,045 | 2/1980 | Bartels | 128/205.24 |
| 4,239,038 | 12/1980 | Holmes | 128/205.24 |
| 4,241,756 | 12/1980 | Bennett et al. | 137/496 |
| 4,333,450 | 6/1982 | Lester | 128/200.14 |
| 4,454,893 | 6/1984 | Orchard | 128/205.24 |
| 4,462,397 | 7/1984 | Suzuki | 128/200.14 |
| 4,463,755 | 8/1984 | Suzuki | 128/204.18 |
| 4,493,339 | 1/1985 | Porter, Jr. | 128/205.24 |
| 4,619,640 | 10/1986 | Potolsky et al. | 128/912 |
| 4,699,137 | 10/1987 | Schroeder | 128/205.24 |

FOREIGN PATENT DOCUMENTS 799225  8/1958  United Kingdom ........... 128/205.24

*Primary Examiner*—Clifford D. Crowder
*Assistant Examiner*—Kimberly L. Asher
*Attorney, Agent, or Firm*—Kay H. Pierce; Mary J. Schnurr

[57] ABSTRACT

A valve for the expiratory tubing of a ventilator circuit. The valve assembly includes a valve body, diaphragm, top cap and control tubing. The valve body includes a valve seat, annular surface, sealing ribs, along with other annular members. The diaphragm includes a thick center portion, connected by a thin web to a relatively thick annular rim and surrounding flange. The top cap includes a compression ring which clamps the diaphragm annular flange to the valve annular surface. In the valve open position, the valve body supports the diaphragm only at the diaphragm flange.

3 Claims, 4 Drawing Sheets

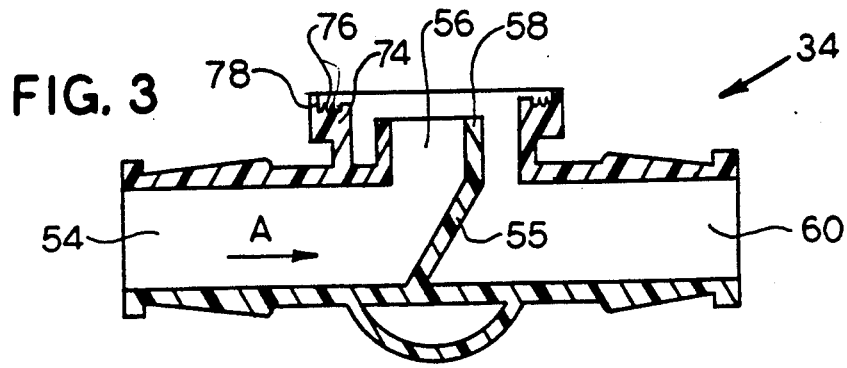
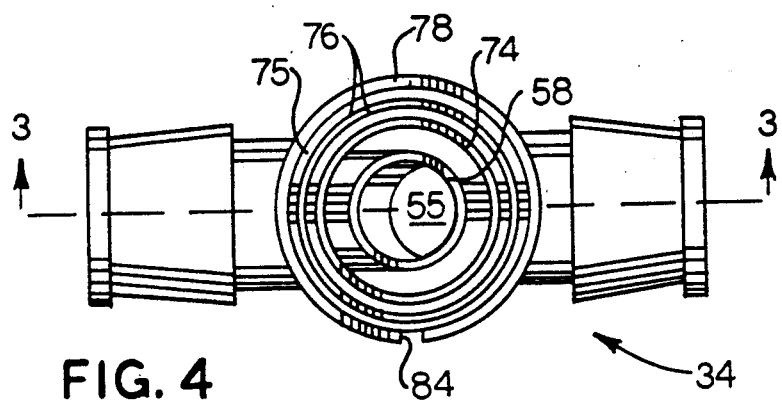
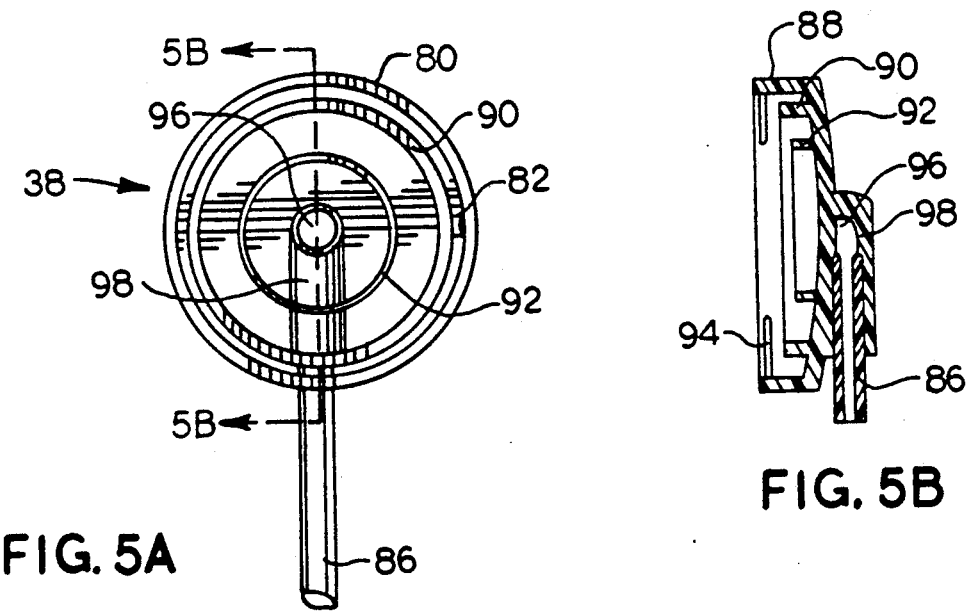

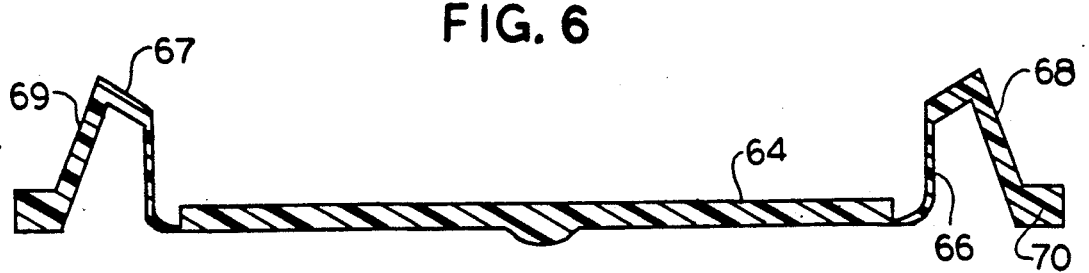
FIG. 6
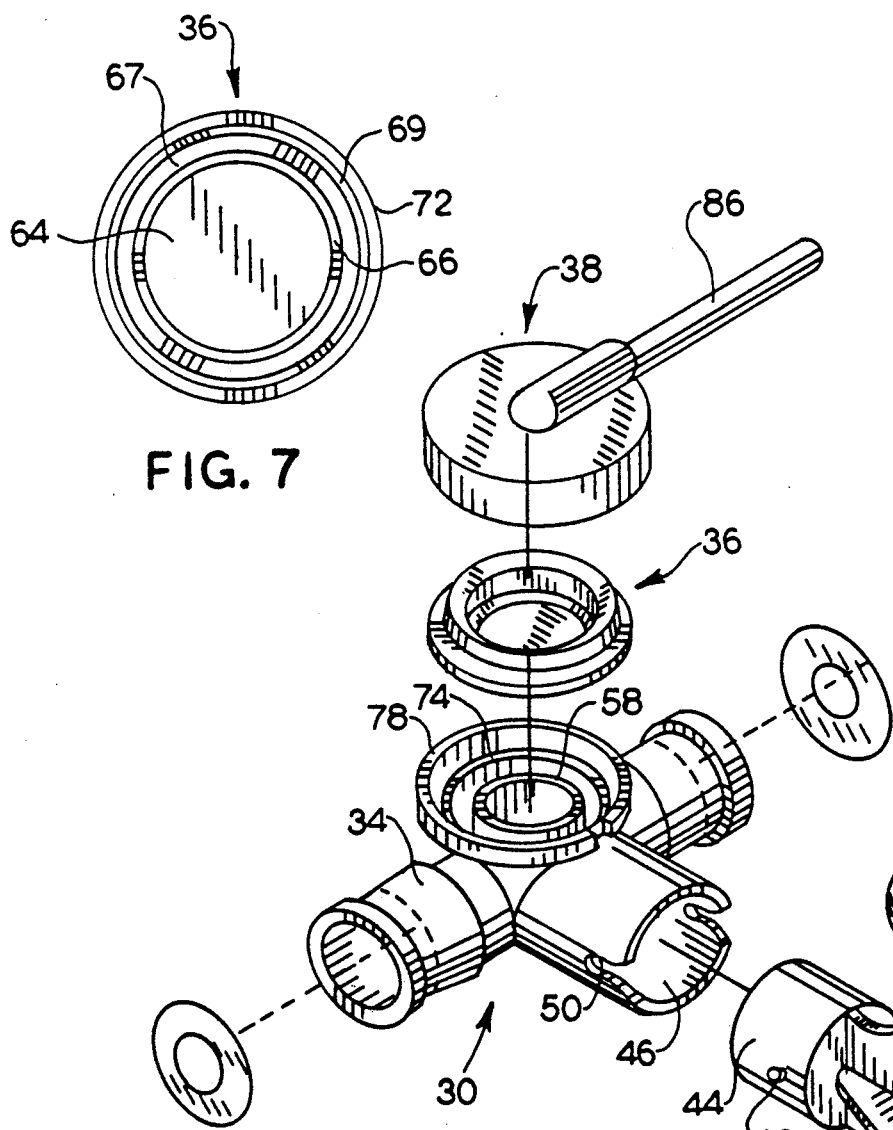
FIG. 7
FIG. 8

EXHALATION VALVE FOR RESPIRATORY CIRCUIT

BACKGROUND OF THE INVENTION

This invention relates to a valve apparatus for the disposable circuit of a mechanical ventilator.

Patients who have respiratory problems often require a mechanical ventilator to aid them in breathing. These ventilators include a disposable breathing circuit to transport the air to and from the patient. Many ventilators utilize a breathing circuit with a exhalation valve in the expiratory limb of the circuit. The exhalation valve closes during the patient's inspiratory phase so that the patient's lungs inflate, and opens during the expiratory phase so that the air may exit the lungs. It is important that the valve completely close the expiratory path during inhalation and yet respond quickly to open the pathway at the appropriate time to allow exhalation.

Some earlier valves do not respond quickly and thus may not open at the appropriate time or may not provide the desired air gap. The patient's lungs must then work harder during exhalation.

Patients with damaged or collapsed lungs sometimes require a positive end expiratory pressure (PEEP), i.e. at the end of the exhalation phase a positive pressure remains in the patient's lungs. The prior valves with slow response times may have particular problems controlling PEEP.

The component of the valve that exerts the greatest control over the valve's performance is the diaphragm. The diaphragm is generally formed of a flexible material. The ease with which this diaphragm is moved into contact with or away from the valve seat governs the valve performance. Many prior valves have a diaphragm with an approximately uniform thickness throughout. These diaphragms generally have a higher resistance to movement and thus they require greater air flow to change their position from closed to open, or vice versa. Since the patient's lungs exert the force that opens the valve, the lungs are required to work harder to provide the additional force necessary to open a prior valve. This is usually undesirable since the patient will recover faster if allowed greater rest.

The present invention provides an improved valve that overcomes or substantially alleviates the problems of the prior art.

SUMMARY OF THE INVENTION

The valve manifold assembly includes a diaphragm seated in a valve body and clamped in place by a top cap. The valve body comprises an annular surface which provides the seal with the diaphragm center portion. The top cap has a compression ring that clamps the diaphragm flange to the valve body.

The diaphragm has a substantially thicker center portion connected by a thin web to an annular rim with a surrounding flange. The web is thinner than either the center portion or the annular rim. The web is connected to the center portion in a coextensive manner and to the annular rim at an angle so that the web forms a curved radius adjacent the center portion. This allows the diaphragm to move more easily and to offer less resistance to a change of position. The valve taught by the present application provides lower resistance to air flow and better pressure control, especially for PEEP.

BRIEF DESCRIPTION OF THE DRAWINGS

FIG. 3 is a cross-sectional view of the valve body taken along lines 3—3 of FIG. 4.

FIG. 4 is a top view of the valve body.

FIG. 5A is a bottom view of the top cap with attached tubing.

FIG. 5B is a cross-sectional view of the top cap taken along lines 5B—5B of FIG. 5A.

FIG. 6 is a cross-sectional view of the diaphragm.

FIG. 7 is a top view of the diaphragm.

FIG. 8 is an exploded perspective view of the valve manifold assembly.

DESCRIPTION OF THE PREFERRED EMBODIMENT

Figure 1:
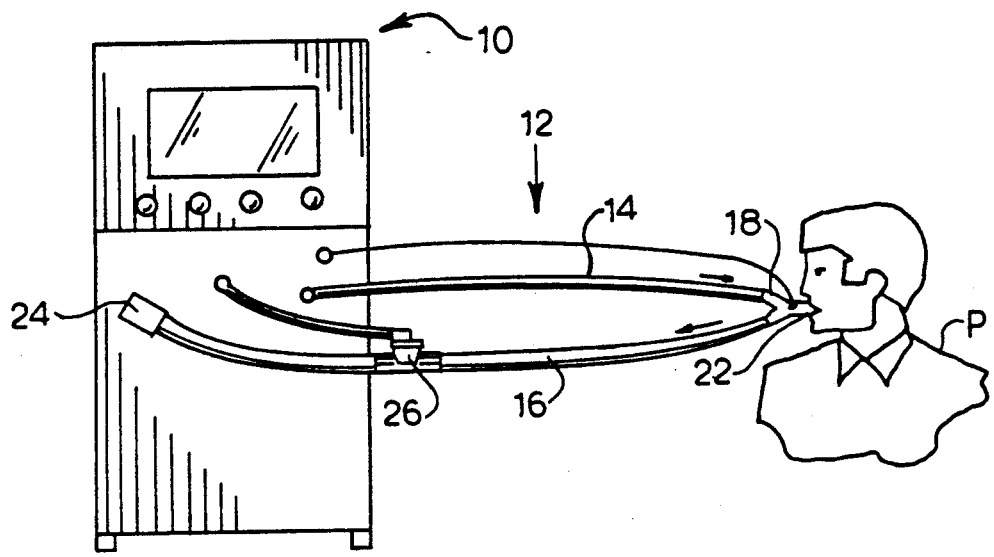
FIG. 1 shows a schematic view of a patient using a mechanical ventilator.
Figure 2:
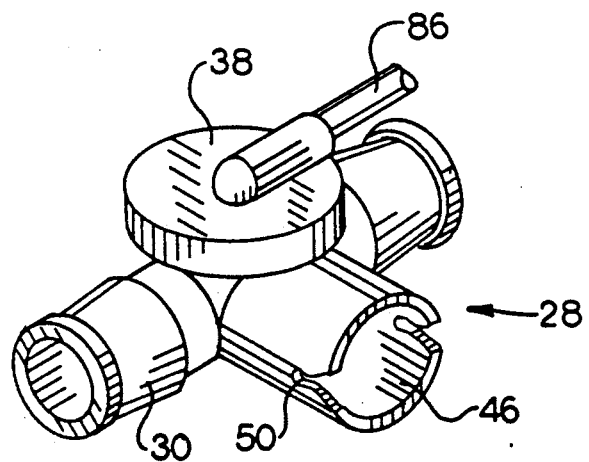
FIG. 2 shows a prospective view of the valve manifold assembly.

FIG. 1 shows a schematic diagram of a patient P using a mechanical ventilator 10. A ventilator breathing circuit 12 connects the patient P to the ventilator 10 and provides for the flow of air to and from the patient. The ventilator circuit 12 comprises inspiratory tubing 14 and expiratory tubing 16 connected together by a wye piece 18. The wye piece is coupled to the patient by a connector 22 which may be of the mask, nasal cannula, or endo-tracheal tube type. The connector 22 shown in FIG. 1 is of the endo-tracheal tube type, by way of example.

The ventilator 10 includes a spirometer 24 that is connected to the end of the expiratory tubing 16 to measure the volume of air exhaled. The ventilator 10 also measures the pressure at the wye piece 18 via measuring tubing 26. Through these two air measurement means, the hospital personnel are able to monitor the breathing of the patient.

The ventilator also provides the air pressure that controls the operation of the exhalation valve through a control tubing 86 connected to the top cap 38 of the valve assembly. The exhalation valve assembly is located on the expiratory tubing at a predetermined distance from the wye piece 18.

FIG. 8 shows an exploded perspective view of the valve manifold assembly, generally indicated as 28. The manifold assembly includes a tubing connector/hangar 32 and a valve assembly 30, which comprises valve body 34, diaphragm 36 and top cap 38.

The tubing connector/hangar 32 includes a split ring 33 that accepts the inspiratory tubing 14 to hold the inspiratory tubing and the expiratory tubing close together during the use of the ventilator. This reduces accidental disassembly of the ventilator system.

The tubing connector/hangar 32 also includes a sphere 42 which fits into a clamp (not shown) on the ventilator 10 to hold the tubing out of the way of the hospital personnel and the patient. The tubing connector/hangar 32 includes a male fitting 44 that mates with the female receptacle 46 of the valve body 34. The male fitting has indicating pins 48 that fit into slots 50 on the valve body 34 to properly orient the tubing connector/hangar 32 with respect to the valve body.

FIG. 3 shows a cross-sectional view of the valve body 34. The air exhaled from the patient moves from left to right as shown in FIG. 3. When the valve is in the open position, the air moves through the inlet 54, past the guiding wall 55, up the vertical channel 56 over the valve seat 58 through the outlet 60 to return to the ventilator.

The guiding wall is not perpendicular to the flow of air in the inlet 54, as with many prior designs. The guiding wall 55 of the present design forms an angle between 90 and 180 degrees with the air flowing in the inlet, designated as arrow A in FIG. 3. For example, in FIG. 3, the angle is approximately 120 degrees. This configuration smooths the flow of air, making the air less turbulent and reducing the effort required by the patient to open the valve.

Figure 10:
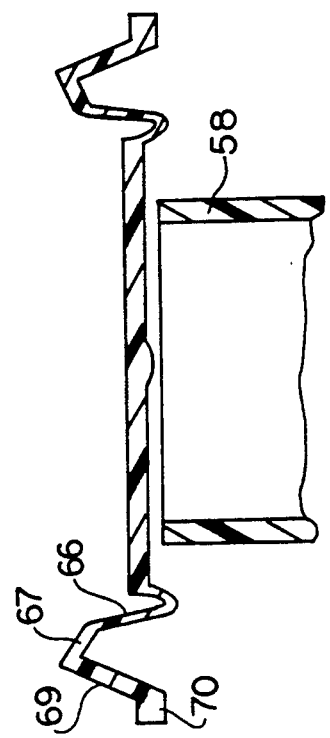
FIG. 10 is a close up cross-sectional view of the diaphragm in the open position.
Figure 9:
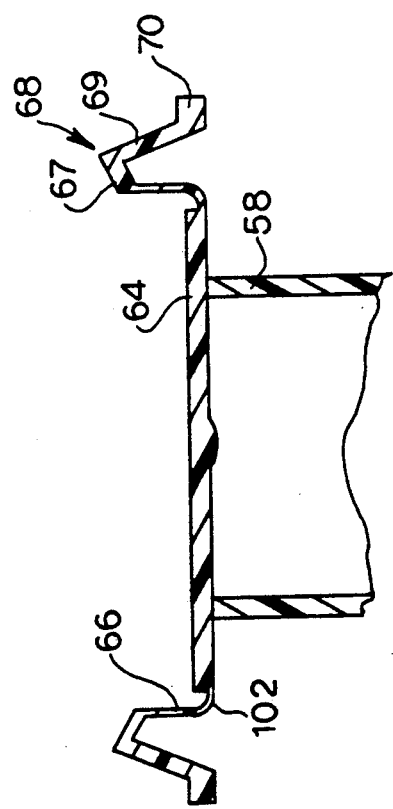
FIG. 9 is a close up cross-sectional view of the diaphragm in the closed position.

During the inspiratory phase, the air pressure in the control tubing 86 pushes the diaphragm 36 into the closed position as shown in FIG. 9. The diaphragm then stops the flow of air in the expiratory tubing and causes the patient's lungs to inflate. During the expiratory phase, the air pressure is withdrawn from the control tubing, allowing the diaphragm to assume the open position as shown in FIG. 10. The patient then exhales to force air through the expiratory tubing 14 and back to the ventilator.

The diaphragm 36 comprises a thickened center portion 64 having a surrounding thin web 66 which connects the center portion to a thickened annular rim 68, as shown in FIG. 6. The annular rim 68 is supported by a horizontal flange 70. The web 66 is coextensive with the center portion 64 so that the bottom of the diaphragm, as shown in FIG. 6, is substantially flat. The annular rim 68 comprises a leg 69 and an extension 67. The rim leg 69 forms an angle with the horizontal flange 70 of 90 degrees or greater, for example 105 degrees as shown in FIG. 6. The rim entension 67 forms an angle with the web 66 of 90 degrees or greater, for example 105 degrees as shown in FIG. 6.

Because of the thin web 66, for example 0.006-0.009 inches, between the two thicker portions of the diaphragm, it is important that the manufacturing process for the diaphragm make consistent parts. By way of example, the other portions the diaphragm may have thicknesses of 0.010 inches for the annular rim extension 67, 0.020 inches for the annular rim leg 69, and 0.027-0.033 inches for the center portion 64. The conventional compressional molding process is not sufficiently consistent. However, a liquid injection molded silicon process makes acceptable parts.

The configuration of the annular rim affects the overall shape of the diaphragm. In the diaphragm relaxed position, the majority of the web 66 is approximately perpendicular to the center portion 64 even though the two portions are connected coextensively and not perpendicularly. When the air pressure is withdrawn from the control tubing 86, the center portion moves upwards away from the valve seat 58. When the patient exhales, the center portion 64 moves farther away from the valve seat 58 and the web 66 adjacent the center portion rolls outward. Because of the small thickness of the web, the diaphragm offers little resistance to change of position.

The shape of the annular rim 68 contributes to the preferred performance of the diaphragm. The present diaphragm reacts to a change of control pressure quickly and yet thoroughly seals the expiratory tubing during the inspiratory phase.

As shown in FIG. 3, the valve body 34 includes a series of annular concentric protuberances: valve seat 58, annular ridge 74, an annular surface 75 having two sealing ribs 76 and a receiving flange 78, in order from the center outwards. The horizontal flange 70 of the diaphragm is positioned inside the receiving flange 78 and on top of the sealing ribs 76. The diaphragm annular rim 68 is positioned above the annular ridge 74 of the valve body at a predetermined distance, while the diaphragm center portion is adjacent the valve body valve seat 58. Prior to being connected to the patient, the diaphragm center portion 64 is positioned 23/1000 inches above the valve seat 58. This preformed gap helps the diaphragm move off of the valve seat 58 after the control air pressure is removed, reducing the force required by the patient to exhale. It is important that the at rest position of the center portion 64 and annular rim 68 are not changed substantially when the diaphragm 36 is clamped within the valve body by top cap 38.

The top cap circumferential edge 88 is of a slightly larger diameter than the valve body receiving flange 78. The circumferential edge has an internal ledge 94 which fits over the bottom 80 of the receiving flange to hold the two parts tightly together. The top cap 38 snap fits over the receiving flange 78 of the valve body 34 and has a internal key 82 which fits within a recess 84 of the receiving flange 78 to properly position the top cap 38 and control tubing 86 with respect to the patient and ventilator.

The top cap 38 also includes a compression ring 90 and a circular reinforcing rib 92. When the top cap 38, diaphragm 36 and valve body 34 are assembled, the compression ring 90 clamps the flange 70 of the diaphragm 36 against the valve sealing ribs 76 to hold the flange 70 in compression. When the diaphragm 36 is closed by air pressure in the control tubing 86, the center portion 64 lays on top of the valve seat 58 to stop the flow of air in the expiratory tubing 16.

When the control air pressure is absent, the diaphragm rests only on its flange 70. In that position, the annular rim leg 69 is positioned above the valve body annular ridge 74 by a predetermined distance. The distance is such that when the valve is closed by control air pressure, the valve body annular ridge 74 prevents the diaphragm annular rim from moving too far into the valve body. It is desirable to prevent excessive movement so that the quick reacting characteristic of the valve is maintained. Thus the compression of the diaphragm flange 70 must be tight enough to prevent air leaks, but not disturb the relationship between the diaphragm and the valve body. The relative heights of the internal ledge 94 of the circumferential edge and the height of the compression ring 90 are arranged to accomplish this goal.

Top cap 38 also includes a central orifice 96 and a tubing connection 98 for the control tubing 86 which provides the control air pressure. The tubing connection 98 is horizontal and provides for an inside fit of the control tubing 86 to reduce the possibility of accidental disconnection.

The ventilator 10 provides air pressure via the control tubing 86 against the center portion 64 of the diaphragm 36 to seal the valve. When the patient exhales, the ventilator removes the control air pressure from the diaphragm 36 to open the expiratory tubing 16. This allows the patient to exhale with little resistance.

The thin web 66 of the diaphragm 36 enables the center portion 64 to be moved with less force. Because the web 66 forms a radial corner 102 instead of a perpendicular wall with the center portion 64 less force is required to move the diaphragm center portion 64 off the valve seat 58. As the center portion 64 of the diaphragm 34 moves off the valve seat 58, the thin web 66 rolls outward, reducing the force required for the patient to exhale. This diaphragm design offers less resistance to flow, allowing the patient to breathe with less effort. The thin web 66 is approximately vertical to also assist in making the center portion 64 easily movable.

While the invention has particularly been shown and described with reference to a preferred embodiment, it will be understood by those skilled in the art that variations in form, construction and arrangement may be made therein without departing from the spirit and scope of the invention.

I claim:

1. A valve for use in an expiratory tube of a ventilator circuit through which expired air flows from a patient comprising:
   a horizontal inlet to receive said flow of expired air;
   a guiding wall downstream from said inlet and disposed at an angle of greater than 90 degrees but less than 180 degrees with respect to said expired air flow at said inlet to smoothly direct said air flow form a horizontal to vertical direction;
   a vertical channel downstream from said guiding wall;
   a valve seat in said vertical channel downstream from said guiding wall;
   a sealing ridge displaced outwardly from said valve seat;
   an outlet downstream from said valve seat;
   a diaphragm having a flange positioned on top of said sealing ridge, said diaphragm having
      a center portion concentrically disposed horizontally within said flange and normally positioned above said valve seat by a gap,
      a thin web connecting said center portion to said flange; and
   means for periodically applying air pressure from a ventilator to said center portion to cause said center portion to seat against said valve seat to close said valve.

2. A valve as recited in claim 1 wherein said web further includes:
   a radial corner extending outwardly from said center portion;
   said thin web extending generally vertically from said radial corner;
   a rim extension extending angularly outwardly from said thin web at an angle of at least 90° degrees; and
   a rim leg extending from said rim extension to said flange and at an angle of at least 90° degrees with said flange, said rim leg and said rim extension being substantially thicker than said thin web so that when said center portion moves away from said valve seat, said thin web moves outwardly.

3. A valve as recited in claim 1, further comprising:
   an annular ridge concentrically disposed between said valve seat and said sealing ridge, said annular ridge being higher than said valve seat and in proximity of said web to limit movement of said web when said center portion of said diaphragm moves against said valve seat.

* * * * *